(12) United States Patent
Clegg et al.

(10) Patent No.: US 7,975,846 B2
(45) Date of Patent: *Jul. 12, 2011

(54) SHARPS HOLDING DEVICE

(75) Inventors: Trent Clegg, Lehi, UT (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 91 days.

This patent is subject to a terminal disclaimer.

(21) Appl. No.: 11/538,767

(22) Filed: Oct. 4, 2006

(65) Prior Publication Data

US 2007/0119740 A1    May 31, 2007

Related U.S. Application Data

(63) Continuation-in-part of application No. 11/290,935, filed on Nov. 30, 2005, now Pat. No. 7,913,841.

(51) Int. Cl.
*B65D 85/24* (2006.01)
(52) U.S. Cl. .................... 206/366; 206/365; 206/370
(58) Field of Classification Search .............. 206/365, 206/366, 369, 370, 382, 571
See application file for complete search history.

(56) References Cited

U.S. PATENT DOCUMENTS

| | | | |
|---|---|---|---|
| 964,406 A | 7/1910 | DeWitt | |
| 4,243,140 A | 1/1981 | Thrun | |
| 4,380,292 A * | 4/1983 | Cramer | 206/366 |
| 4,919,264 A | 4/1990 | Shinall | |
| 4,936,449 A * | 6/1990 | Conard et al. | 206/366 |
| 5,265,724 A | 11/1993 | Dondlinger | |
| 5,311,985 A * | 5/1994 | Suida | 206/210 |
| 5,417,505 A * | 5/1995 | Voorhees | 401/208 |
| 5,462,163 A * | 10/1995 | Berry | 206/370 |
| 5,538,132 A | 7/1996 | Propp et al. | |
| 5,626,230 A * | 5/1997 | Shanley et al. | 206/571 |
| 5,850,917 A | 12/1998 | Denton et al. | |
| 5,967,778 A | 10/1999 | Riitano | |
| 5,975,295 A | 11/1999 | Diamond | |
| 6,279,743 B1 | 8/2001 | Ballard et al. | |
| 6,530,479 B2 * | 3/2003 | Hernandez | 206/572 |
| 6,827,212 B2 | 12/2004 | Reaux | |
| 7,070,051 B2 | 7/2006 | Kanner et al. | |
| 7,159,714 B2 * | 1/2007 | Wilkinson et al. | 206/366 |
| 2003/0024891 A1 | 2/2003 | Diamond | |

(Continued)

OTHER PUBLICATIONS

Office Action dated Nov. 27, 2009 for U.S. Appl. No. 11/538,761.

(Continued)

*Primary Examiner* — Jila M Mohandesi
*Assistant Examiner* — Sharon M Prange
(74) *Attorney, Agent, or Firm* — Stoel Rives LLP

(57) ABSTRACT

A sharps holding device according to the present invention may include a body providing a housing having a contact surface and at least one needle securement aperture. A needle securement aperture may be configured to allow insertion of at least a portion of a needle or other sharp into the housing. The device may also have one or more needle cushions positioned adjacent to the contact surface. A needle cushion may be configured such that a needle or other sharp inserted through a securement aperture can be inserted into the needle cushion. A lid may be included in the device and configured to secure the one or more needle cushions within the body of the housing. One or more needle cushions may be cooperatively engaged by the contact surface of the body and the lid, and one of the needle cushions may be located between the lid and the contact surface.

14 Claims, 5 Drawing Sheets

U.S. PATENT DOCUMENTS

2007/0119738 A1    5/2007    Clegg et al.
2007/0119739 A1    5/2007    Clegg et al.

OTHER PUBLICATIONS

Office Action dated Jan. 22, 2009 for U.S. Appl. No. 11/538,761.
Office Action dated Dec. 28, 2009 for U.S. Appl. No. 11/290,935.
Office Action dated Mar. 31, 2009 for U.S. Appl. No. 11/290,935.
Office Action dated Jul. 9, 2008 for U.S. Appl. No. 11/290,935.
International search report and written opinion for PCT/US2006/061355 dated Nov. 29, 2006.
Office Action dated Aug. 3, 2010 for U.S. Appl. No. 11/290,935.
Notice of Allowance dated Jul. 13, 2010 for U.S. Appl. No. 11/538,761.
Notice of Allowance dated Feb. 10, 2011 for U.S. Appl. No. 11/290,935.

* cited by examiner

SHARPS HOLDING DEVICE

CROSS-REFERENCE TO RELATED APPLICATIONS

This application is a continuation-in-part of U.S. patent application Ser. No. 11/290,935, filed Nov. 30, 2005, which is incorporated herein by reference in its entirety. This application also incorporates by reference in its entirety U.S. patent application Ser. No. 11/538,761 filed Oct. 4, 2006.

BACKGROUND OF THE INVENTION

The present invention relates to a temporary instrument holder. In more particular, the present invention relates to a temporary holder for medical instruments, such as needles, trocars, scalpels or other devices or implements. The temporary holder includes a lateral instrument holder aperture.

In recent years, increased attention has been directed by medical practitioners and the medical community as a whole to blood borne illnesses and infections. The potential for the transmission of blood borne illnesses from patients to practitioners has heightened the awareness of safety standards to protect against inadvertent practitioner infection. A variety of new safety practices and regulations have been developed dictating procedures to be followed before, during, and after surgery as well as during the routine care of patients. For example, special procedures and cautions are recommended and/or required for interactions with patients involving bodily fluids, the handling of medical apparatus that have been utilized in connection with the bodily fluids of patients, and for the disposal of bodily fluids and other biological materials.

As a part of the new safety emphasis with regard to blood borne illnesses and infections, particular attention has been directed to the handling of needles, trocars, or other "sharps." Such sharps have been a subject of increased focus due to the potential for accidental puncture of the practitioner's skin and consequent transmission of disease to the practitioner. A number of devices have been developed to protect against accidental punctures while utilizing sharps. For example, self-deploying needle shields, which can be readily actuated with limited risk of inadvertent puncturing of a practitioner, have been provided on a number of needles and other trocar type apparatus. Specialized depositories for the receipt and containment of used needles have also been developed which provide for safe and simple disposition of sharps.

Another type of device which has been developed to prevent needle sticks or other punctures of a practitioner are temporary needle holders. Such temporary needle holders are adapted to be utilized in a surgical field for holding a needle or other sharp implement that has been utilized or is intermittently utilized during the course of the procedure. Such temporary needle holders typically have a needle holder field in which the needles can be inserted while they are not being used. The temporary needle holder provides a location for the holding of needles that are not being utilized, such that the needles are not left on the surgical surface in a manner that they may inadvertently stick or puncture the skin of a practitioner during the course of the procedure.

Typically, such temporary needle holders are configured to be fairly small. Smaller temporary needle holders are typically desired due to surgical surface ergonomics and the fact that a limited number of needles are typically utilized in a procedure. For example, typically the number and types of surgical tools, implements, and containers placed in the surgical field for use during the procedure are sufficient that a limited amount of space is available for each apparatus. Due to the limited number of needles that are utilized in typical procedures, a fairly small temporary needle holder is sufficient to hold the number of needles needed during the procedure. Because a fairly small number of needles are typically utilized and the size requirements for additional needles are quite minimal, a larger unit is typically inefficient due to unused space on the needle holder field. Elimination of unused space on the needle holder field typically creates greater efficiencies in usage of materials, storage/shipping size, and per unit weight.

One problem associated with such smaller and/or lighter devices, is that where a practitioner is utilizing a larger needle and syringe combination or a partially-filled syringe, placement of the needle and syringe in the temporary needle holder can result in disadvantageous tipping of the temporary needle holder. Not only can such tipping be unpredictable, but the tipping can make it difficult to utilize the temporary needle holder and the needles and/or syringes positioned therein during the course of the procedure. Additionally, tipping of a partially-filled syringe can result in turbulence in the contents of the syringe that may introduce air bubbles into the syringe. As a result, valuable surgical time may be consumed de-bubbling the syringe in preparation for injection of the contents of the syringe into the patient.

What is needed is a sharps holder large enough to prevent accidental damage or disruption of surgical instruments, while still being useful in the operating environment.

BRIEF SUMMARY OF EMBODIMENTS OF THE INVENTION

Throughout the specification, "sharps" is used to describe any instrument or device that poses a contamination risk to people, such as medical personnel, by disruption of the skin. Examples of sharps may include, but are not limited to, sharp instruments such as needles, trocars, scalpels, and other dangerous implements with edges or surfaces that can cut or puncture.

In one embodiment of the present invention, a sharps holding device includes a housing having a contact surface and at least one instrument securement aperture. An instrument securement aperture may be configured to allow insertion of at least a portion of a needle or other sharp into the housing. The device may also have one or more cushions positioned adjacent to the contact surface. A cushion may be configured such that a needle or other sharp inserted through a securement aperture can be inserted into and held by the cushion. Additionally, a selectively closeable bottom member may be included in the device and configured to secure the one or more instrument cushions within the housing. One or more cushions may be cooperatively engaged by the contact surface of the housing and the bottom member. At least one of the cushions may be located between the lid member and the contact surface.

The lid may also be moveably connected to the housing with a hinge. One or more securement apertures may be located on various surfaces of the body, including a surface opposite the lid. The device may also include a planar member configured to securely attach to the body.

These and other aspects of the present invention will become more fully apparent from the following description and appended claims.

BRIEF DESCRIPTION OF THE DRAWINGS

To further clarify the above and other aspects of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Figure 1A:
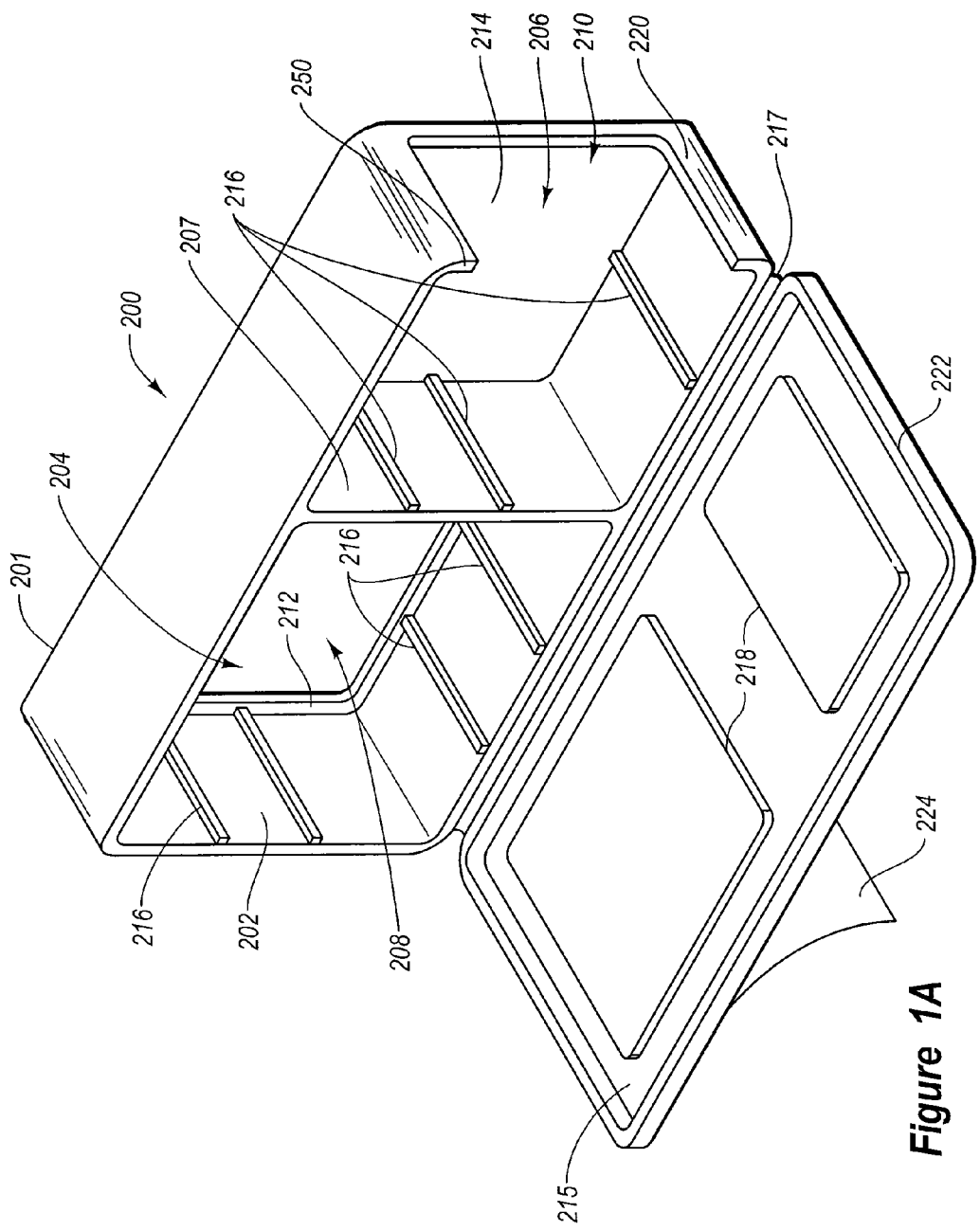
FIG. 1A is an isometric view of a portion of the sharps holder apparatus, according to an embodiment of the present invention.
Figure 1B:
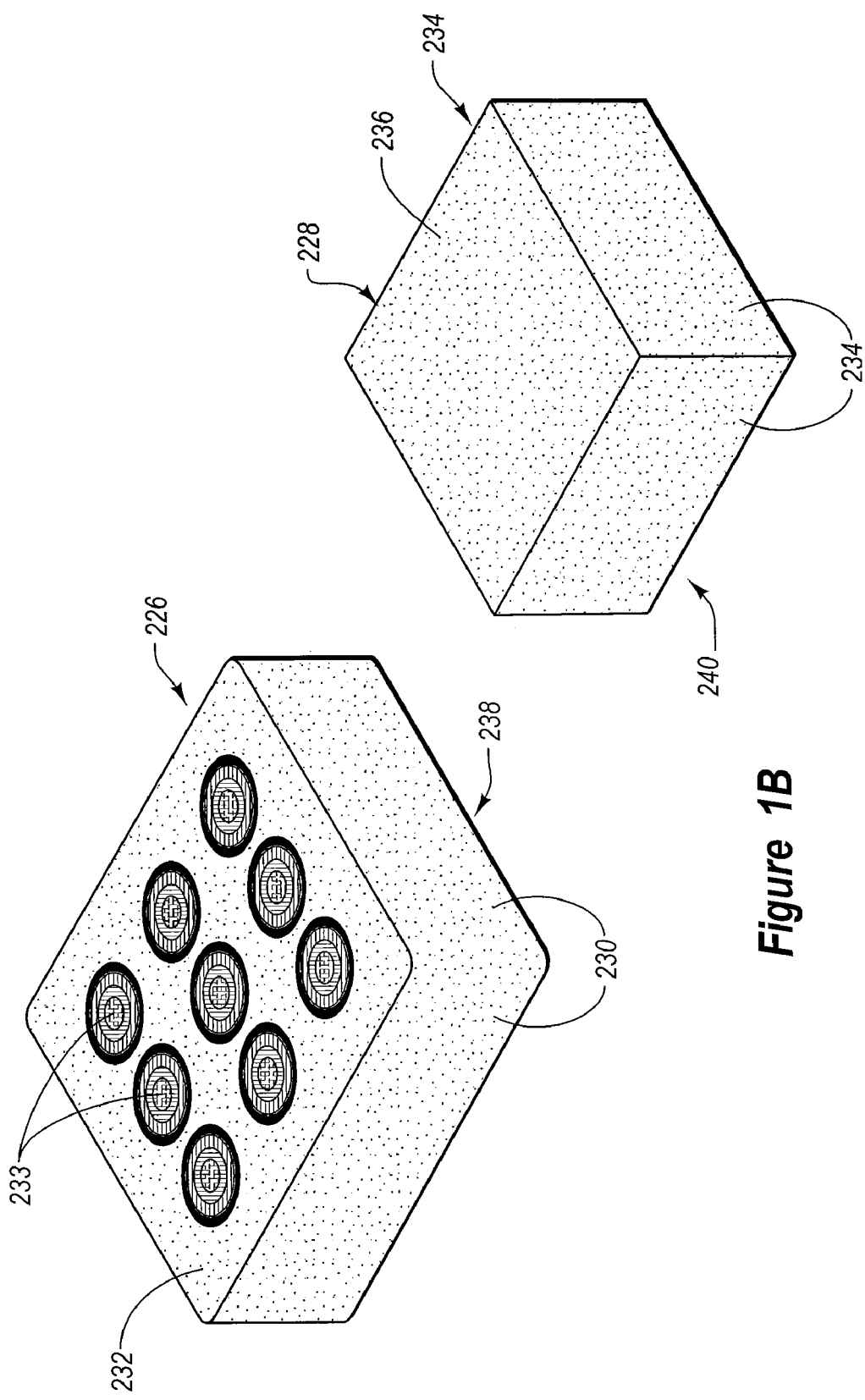
FIG. 1B is an isometric view of a portion of the sharps holder apparatus, according to an embodiment of the present invention.

FIGS. 1A and 1B disclose various elements of the sharps holder apparatus, according to one embodiment of the present invention. In the illustrated embodiment, the sharps holder apparatus 200 comprises a housing 201, a top surface cushion layer 226, and a side-surface cushion layer 228. Top surface cushion layer 226 and side surface cushion layer 228 can be positioned within housing 201 to provide a mechanism for capturing needles, sharps, syringes, or other sharp medical implements that may be utilized within the surgical field. Housing 201 may provide a mechanism for accommodating and securing top surface cushion layer 226 and side surface cushion layer 228 in a manner that allows for securement of the sharps by cushion layers 226 and 228.

In the illustrated embodiment, housing 201 may include an outer wall 202, a first cavity 204, a second cavity 206, a boundary septum 207, a top surface aperture 208, a side surface aperture 210, and a moveable bottom member 215.

Outer wall 202 can define the outer boundary of housing 201 and provides a secure framework in which top surface cushion layer 226 and side surface cushion layer 228 can be positioned. Outer wall 202 partially defines a first cavity 204 and a second cavity 206. First cavity 204 may have a substantially square configuration having a depth configured to accommodate top surface cushion layer 226. Second cavity 206 may have a depth and size to accommodate second side surface cushion layer 228. Boundary septum 207 can separate first cavity 204 from second cavity 206. Utilizing a boundary septum 207 prevents passage of a trocar, needle, or other sharp implement between top surface cushion layer 226 and side surface cushion layer 228.

Figure 2B:
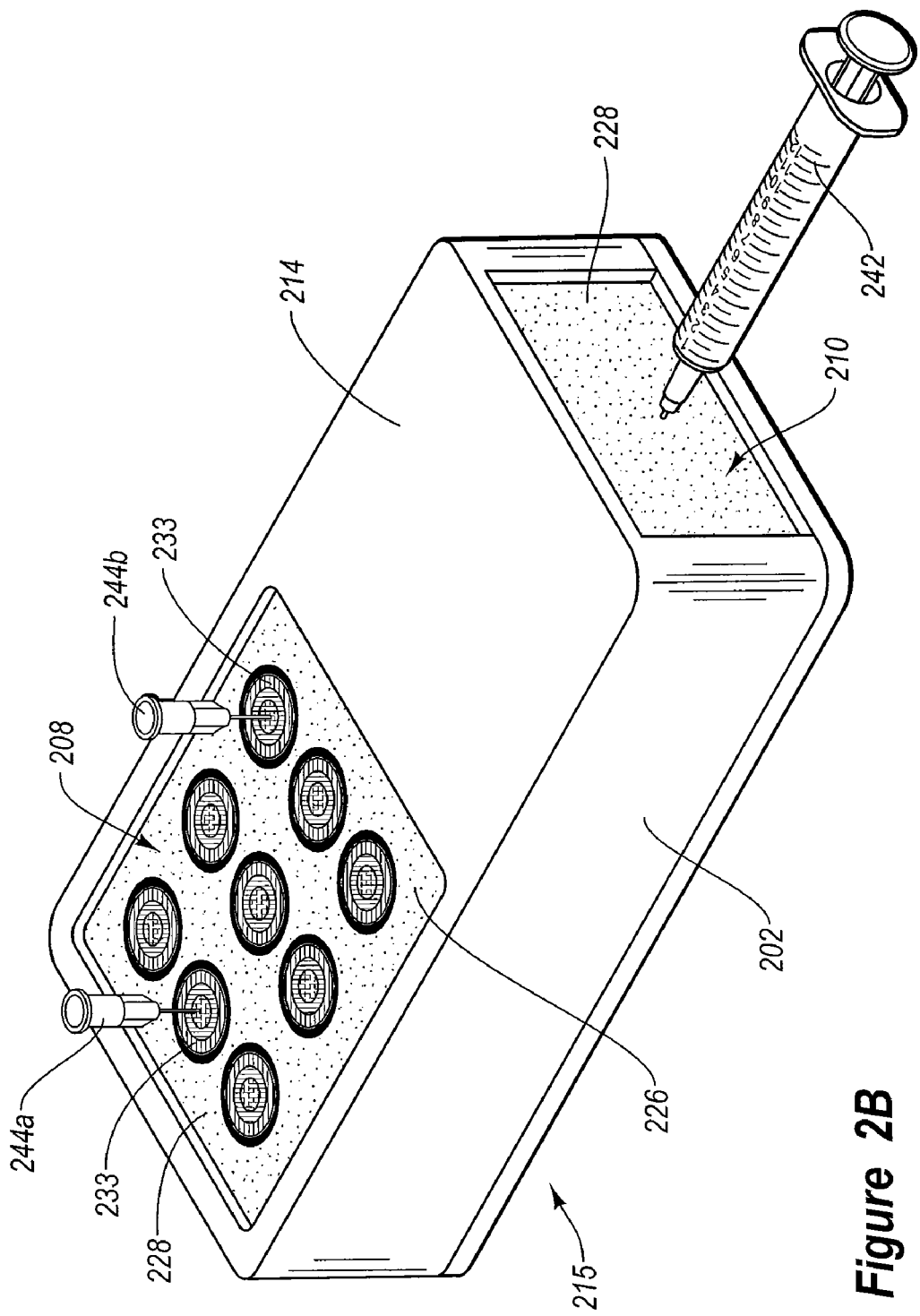
FIG. 2B is a view of a fully assembled sharps holder apparatus, including depictions of sharps, according to an embodiment of the present invention.
Figure 3:
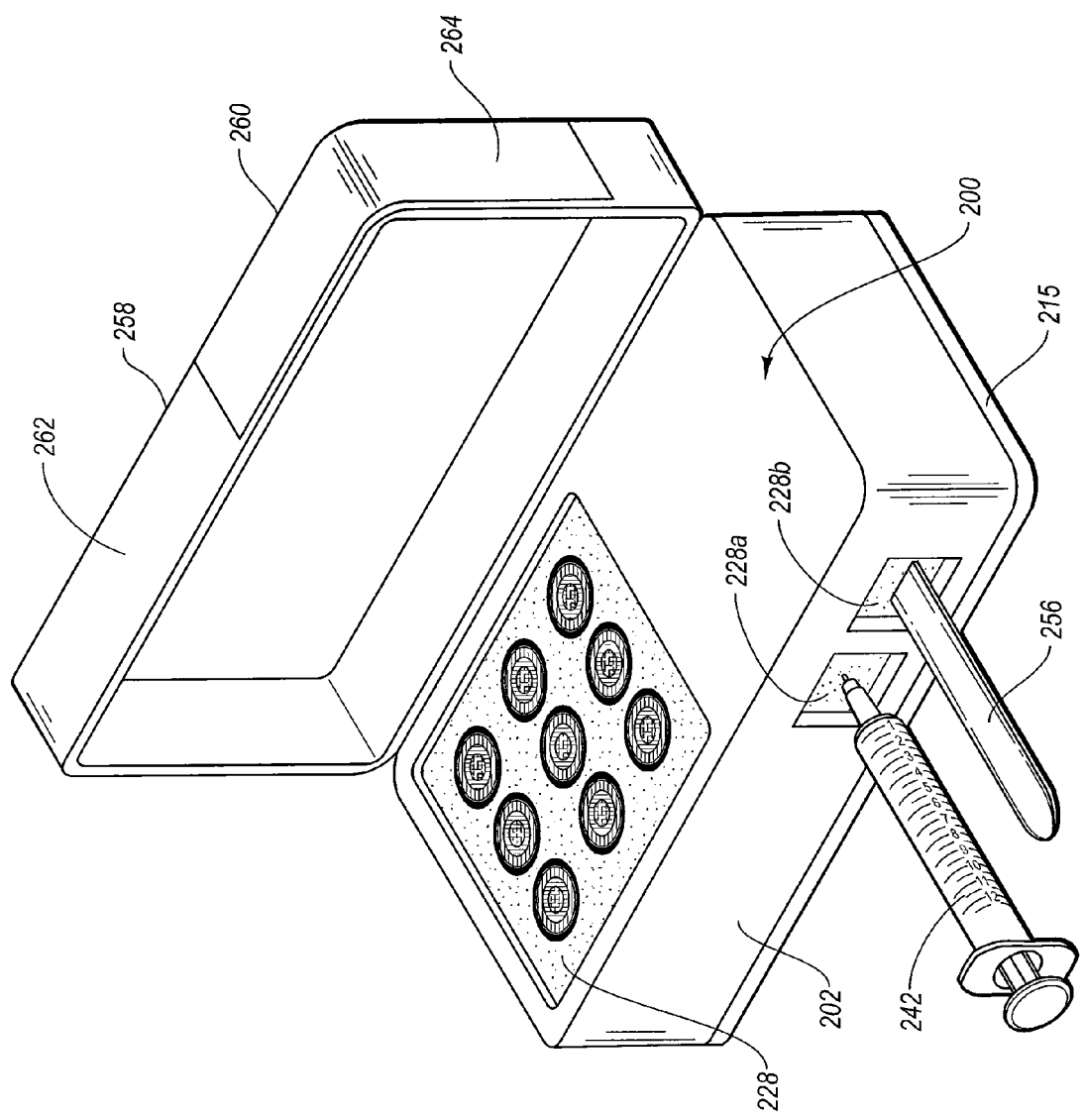
FIG. 3 is a perspective view of a sharps holder apparatus according to an embodiment of the present invention

As illustrated, housing 201 may include a top surface aperture 208 and side surface aperture 210. Top surface aperture 208 is defined by the top surface of housing 201. Side surface aperture 210 may be positioned on the side surface of housing 201. When sharps holder apparatus 200 is fully assembled and resting on the surgical surface, top surface aperture 208 may then be positioned upward allowing needles, trocars, or other instruments to be inserted therein, as illustrated in FIG. 2B. As shown in FIG. 3, side surface aperture 210 may be positioned on the side of the needle holder apparatus in a manner such that heavier or larger implements, such as a fluid-filled syringe 242, a scalpel 256, or other implement can be positioned in the side surface cushion layer 228 while the instrument, trocar, or other apparatus can rest on the table or other surgical surface in manner to prevent tipping of the needle holder apparatus.

A top rim contact surface 212, top barrier surface 214, and side rim contact surfaces 250 are also illustrated. Top rim contact surface 212, top barrier surface 214, and side rim contact surface 250 facilitates proper positioning and securement of top surface cushion layer 226 and side surface cushion layer 228 during assembly. For example, when top surface cushion layer 226 is positioned in first cavity 204, top surface cushion layer 226 may be slid into first cavity 204 until the outer rim of the upper surface of top surface cushion layer 226 contacts rim contact surface 212. Contact surface 212 can stop additional upward movement of top surface cushion layer 226, and also provides indication to the user that further advancement of the top surface cushion layer is no longer necessary.

Top barrier surface 214 may provide a solid contact surface that also stops further advancement of side surface cushion layer 228 when side surface cushion layer 228 is being inserted into housing 201. Side rim contact surfaces 250 may maintain the lateral positioning of side surface cushion layer 228 in second cavity 206. In this manner, side surface cushion layer may be prevented from migrating out of side surface aperture 210 during assembly or usage of the needle holder apparatus.

A moveable bottom member 215 is also illustrated. Moveable bottom member 215 may be configured to be secured to the bottom periphery of outer wall 202 to secure top surface cushion layer 226 and side surface cushion layer 228 within their respective cavities 204 and 206. As illustrated, moveable bottom member 215 may be attached to one side of outer wall 202 using a hinge 217. In this manner, the desired positioning of moveable bottom member 215 relative to the other portions of housing 201 may be maintained until the top surface cushion layer 226 and side surface cushion layer 228 have been positioned within first cavity 204 and second cavity 206.

Once top surface cushion layer 226 and side surface cushion layer 228 have been positioned within housing 201, the user can simply hinge moveable bottom member 215 into cooperative and locked engagement with the entire bottom periphery of outer wall 202. As illustrated, outer wall 202 includes a snap fit ridge 220 and moveable bottom member 215 includes a snap fit flange 222. When moveable bottom member 215 is hinged to a closed position relative to outer wall 202, snap fit flange 222 biases over snap fit ridge 220 securing moveable bottom member 215 in position relative to the other components of housing 201. In this manner, top surface cushion layer 226 and side surface cushion layer 228 can be secured within housing 201 in a relatively simple, effective, and cost effective manner.

As illustrated, side margin supports 216 and bottom margin supports 218 may be provided. Side margin supports 216 comprise a raised ridge, and bottom margin supports 218 comprise raised panels. Side margin supports 216 and bottom margin supports 218 may be adapted to contact portions of top surface cushion layer 226 and side surface cushion layer 228. Side margin supports 216 and bottom margin supports 218 may effectively secure top surface cushion layers 226 and side surface cushion layer 228 within first cavity and second cavity 204 and 206, even when there is a slight margin left by a discrepancy between the size of top surface cushion layer 226 and first cavity 204 or side surface cushion layer 228 and second cavity 206. In this manner, any gap that is left by a slightly smaller side of cushion layers 226 and 228 may be effectively filled, while allowing for larger cushion layers to also be inserted within first cavity 204 and second cavity 206.

As illustrated, side margin supports 216 may be positioned on the inside of first cavity 204 and second cavity 206. For example, side margin supports 216 can be provided on each of the four lateral surfaces along outer wall 202 and boundary septum 207. The somewhat narrow and stiffened nature of side margin supports 216 and bottom margin supports 218 may allow for a certain amount of deformation of cushion layers 226 and 228 in the event that there is little or no margin between the sides of the cushion layer and the respective cavity in which it is being positioned. Additionally, the ridged nature of side margin supports 216 and bottom margin supports 218 may allow for securement of the cushion layer in the event that there is a somewhat larger margin between the sides of the cushion layer and the respective cavity in which it is positioned.

Side margin supports 216 may be configured to fill lateral discrepancies in size between the cushion layer 226, 228, and the cavities 204 and 206, respectively. Bottom margin supports 218 may be configured to facilitate contact between top rim contact surface 212 and the top surface cushion layer 226. Similarly, bottom margin support 218 may facilitate contact between top barrier surface 214 and the side surface cushion layer 228.

As illustrated, an adhesive cover strip 224 may extend from the underside of moveable bottom member 215. Adhesive cover strip 224 includes a tab that can be grasped by a user facilitating removal of adhesive cover strip 224 from the respective adhesive strip. When positioned on the underside of moveable bottom member 215, adhesive cover strip 224 may secure sharps holder apparatus 200 on a surgical or other support surface, minimizing tipping or inadvertent movement of the apparatus during a surgical procedure being performed.

Top surface cushion layer 226 and side surface cushion layer 228 are depicted in FIG. 1B. As illustrated, top surface cushion layer 226 may include a side surface 230 and a top surface 232. As previously discussed, side surface 230 may be positioned in contact with outer wall 202 and boundary septum 207. Top surface 232 may be largely exposed to the external working environment by top surface aperture 208 of housing 201. In this manner, top surface 232 can be accessed by a user for positioning needles, trocars, scalpels, or the like within the sharps holder apparatus. The outer periphery of top surface 232 may be configured to contact top rim contact surface 212 to secure the positioning of top surface cushion layer 226 within housing 201. Top surface cushion layer 226 also includes a bottom surface 238. Bottom surface 238 may be configured to be in contact with moveable bottom member 215 so that top surface cushion layer 226 is thereby cooperatively secured between top rim contact surface 212 and bottom surface 238.

In the illustrated embodiment, a plurality of targets 233 of top surface cushion layer 226 are depicted. Targets 233 are positioned on top surface 232 of top surface cushion layer 226. Targets 233 may provide a visual identification facilitating proper insertion of needles, trocars, or other instruments within the top surface cushion layer 226.

As illustrated, a side surface cushion layer 228 is also depicted. Side surface cushion layer 228 includes a side surface 234, a top surface 236, and bottom surface 240. As previously discussed, top surface 236 may be configured to be in contact with a top barrier surface 214. One of side surfaces 234 may be exposed to the external environment by side surface aperture 210. In this manner, a practitioner, such a surgeon or nurse, can insert a scalpel, fluid filled syringe, or other instrument into side surface cushion layer 228. In this manner, when moveable bottom member 215 is resting on the support surface, the instrument positioned within side surface cushion layer 228 can rest on the surgical surface in a manner to prevent tipping of the needle holder apparatus or inadvertent breakage of the instrument positioned within side surface cushion layer 228.

As illustrated, bottom surface 240 may be positioned in contact with moveable bottom member 215. In this manner, side surface cushion layer 228 may be sandwiched between top barrier surface 214 and moveable bottom member 215.

As will be appreciated by those skilled in the art, a variety of types and configurations of the sharps holder apparatus can be implemented without departing from the scope and spirit of the present invention. For example, according to one embodiment of the present invention, a single needle cushion layer may be provided. In another embodiment, the moveable bottom member may be locked into place once the sharps holder apparatus has been fully assembled. In another embodiment, moveable bottom member may be secured to the needle holder apparatus using other than a hinge. In another embodiment, the moveable bottom member may not be secured to the needle holder apparatus but positioned in place once the one or more cushion layers have been positioned within the housing. In yet another embodiment the moveable bottom member may comprise a plurality of components, which cooperatively secure one or more cushion layers within the housing. In yet another embodiment, one or more side ports may be provided in addition to a top surface cushion layer.

Figure 2A:
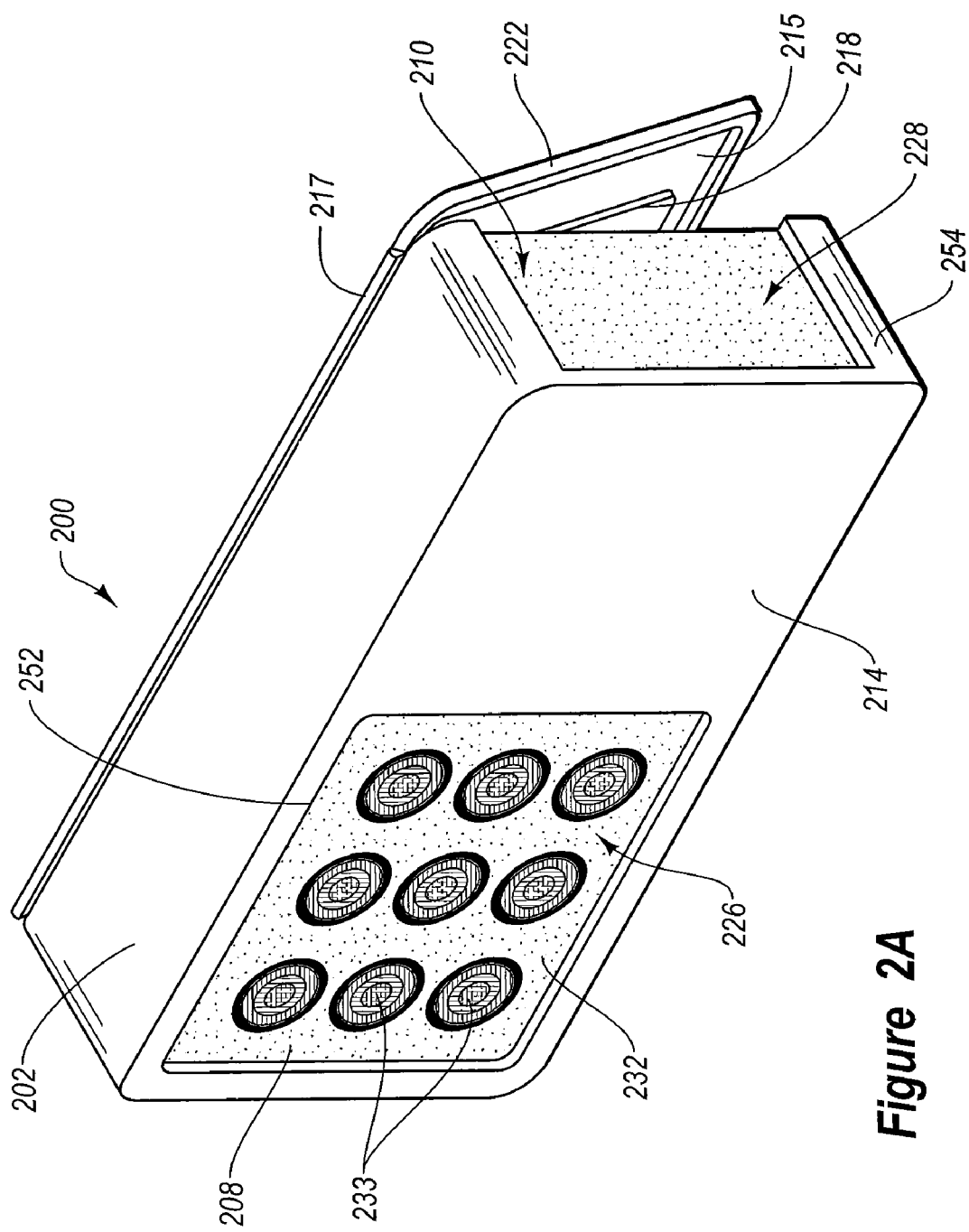
FIG. 2A is a view of a partially assembled sharps holder apparatus, according to an embodiment of the present invention.

FIG. 2A is a top perspective view of sharps holder apparatus 200 during assembly. In the illustrated embodiment, top surface cushion layer 226 may be positioned within housing 201. As previously discussed with reference to FIGS. 1A and 1B, top surface cushion layer 226 may be configured to be positioned within first cavity 204 (see FIGS. 1A and 1B). As illustrated, top surface cushion layer 226 may be fully advanced within housing 201 such that top surface cushion layer 226 is accessible through top surface aperture 208. A plurality of targets 233 may be seen through top surface aperture 208. In this manner, potentially desired points of contact between the needle and the top surface cushion layer 226 are clearly displayed to the user. A top rim 252 is also illustrated. Top rim 252 may be positioned on the upward facing side of the top rim contact surface 212 depicted in FIG. 1A. Top rim 252 may have a desired amount of elevation over and above top surface 232 of top surface cushion layer 226.

As illustrated, side surface cushion layer 228 may be fully advanced within second cavity 206 (see FIGS. 1A and 1B). Side surface cushion layer 228 may be in contact with top barrier surface 214. Additionally, a side rim 254 may be in contact with a side surface 236 of side surface cushion layer 228. In this manner, inadvertent migration of side surface cushion layer 228 out through side surface aperture 210 may be prevented. Side surface aperture 210 may provide access to side surface cushion layer 228. In this manner, practitioner can insert needles, syringes, scalpels, or other medical devices into the side port of the needle holder apparatus. In this manner, heavier items, such as a fluid-filled syringe, scalpel, or other instrument can rest on the table to prevent inadvertent breakage or damage to the medical instrument which is inserted into side surface cushion layer 228.

In the depicted embodiment, the movable bottom member 215 is starting to be closed in relation to the other components of housing 201. As previously discussed, movable bottom member 215 may be secured to housing 201 utilizing a hinge 217. Snap fit flange 222 on the outer periphery on a portion of movable bottom member 215 may allow for securement of the movable bottom member 215 to snap fit ridge 220 of housing 201 (see FIGS. 1A and 1B). In this manner, when movable bottom member 215 is closed, the fit between snap fit ridge 220 and snap fit flange 222 may effectively secure movable bottom member 215 to the other components of the housing securing the position of top surface cushion layer 226 and side surface cushion layer 228. A bottom margin support member 218 is also shown. The illustrated bottom margin support 218 may be configured to contact side surface cushion layer 228 to ensure a desired fit between side surface cushion layer, top barrier surface 214, and movable bottom member 215.

FIG. 2B illustrates needle holder apparatus 200 during use. In the illustrated embodiment, the movable bottom member 215 may be secured to the other components of housing 201. In this manner, top surface cushion layer 226 and side surface cushion layer 228 may be secured within housing 201 to allow for desired operation of the sharps holder apparatus.

A needle syringe combination 242 is depicted as being inserted into side surface cushion layer 228. As illustrated, the needle syringe combination may include an amount of fluid which adds substantially to the weight of needle syringe combination 242. In the event that needle syringe combination 242 were inserted into top surface cushion layer 226, the weight of needle syringe combination 242 could tip the needle holder apparatus or inadvertently result in breakage of the needle portion of the needle syringe combination 242. In the illustrated embodiment, needle syringe combination 242 can rest on the surgical surface on which the needle holder apparatus is positioned. In this manner, positioning of the needle syringe combination 242 is maintained until the needle syringe combination needs to be utilized again or until the entire needle holder apparatus, including the needle syringe combination 242, is disposed.

As illustrated, needle tips 244a and 244b may be positioned within the top surface cushion layer 226. In the illustrated embodiment, a first needle tip 244a may be positioned within a first target 243 and a second needle tip 244b also positioned within a different target 243. In this manner, the practitioner can quickly identify potential open areas where needle tip or other sharp implement can be inserted. Additionally, the practitioner can quickly identify the amount of remaining space for sharps that are used in connection with subsequent portions of the procedure.

The top barrier surface 214 may be provided to prevent inadvertent insertion of a needle or other sharp implement into the top surface 236 (not shown) of side surface cushion layer 228. In this manner, inadvertent migration of a needle tip through top surface 236 of side surface cushion layer 228 and out through side surface aperture 210 may be prevented.

FIG. 3 is a perspective view of sharps holder apparatus 200 according to another illustrative embodiment of the present invention. In the illustrated embodiment, first and second side surface cushion layers 228a and 228b are illustrated. By providing first and second side surface cushion layers 228a and 228b, a plurality of different medical instruments may be inserted into the needle holder apparatus organized in an efficient manner. For example, as illustrated, a needle syringe combination 242 may be inserted into side surface cushion layer 228a. Scalpel 256 may also be positioned in side surface cushion layer 228b. In this manner, interference or inadvertent breakage by contact between needle syringe combination 242 and scalpel 256 may be prevented. According to one embodiment of the present invention, side surface cushion layers 228a and 228b may comprise a single internal piece of foam which may be simply separated by a single septum member (not shown) in the outer wall of housing 201. In other words, first and second lateral surface apertures may be provided to access a single side surface to cushion layer positioned on the interior of housing 201.

As illustrated, a lid 256 may be provided. Lid 256 may be configured to be positioned over sharps holder apparatus 200 subsequent to usage of the sharps holder apparatus 200 and in preparation for disposal of the apparatus and the needles, syringes, or other medical implements utilized therewith. As illustrated, lid 258 may include a top surface 260, a sidewall 262, and an expandable drape 264. Top surface 260 may comprise a hardened material which minimizes inadvertent puncture by implements that are positioned within needle holder apparatus. Sidewall 262 may provide an amount of displacement between the upper surface of the top surface cushion layer 226 and top surface 260.

An expandable drape 264 may also be provided along a portion of lid 258. Expandable drape 264 may be deployed subsequent to closing of lid 258. Expandable drape 264 may be made of a material that allows expandable drape 264 to extend past and enclose components positioned in side surface cushion layers 228a and 228b. Similarly, expandable drape may include several pleats that allow expansion in a similar manner. Alternatively, the expandable drape 264 may not entirely enclose the components positioned within side cushion layer 228 that are utilized to secure those components in place during disposal of the needle holder apparatus, but may expand to contact any components positioned within side cushion layer 228 and provide additional stability to the components.

As will be appreciated by those skilled in the art, a variety of types and configurations of sharps holder apparatus can be utilized without departing from the scope and spirit of the present invention. According to one embodiment of the present invention, the lid 258 may include an extension portion which secures part or all of the apparatus positioned within the side surface cushion layers. In another embodiment, needle holder apparatus may include only side ports and does not include a top surface for inserting needles, trocars, syringes, or the like. In yet another embodiment, the side surface cushion layers may include targets facilitating the insertion of instruments into a central or desired location within the side surface cushion layers.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
    a housing including:
        a contact member,
        a first wall member extending perpendicular from the contact member,
        a second wall member extending perpendicular from the wall contact member and the first wall member,
        a third wall member parallel to the first wall member, and
        a fourth wall member parallel to the second wall member, wherein
    the contact member and the wall members define a volume;
    a bottom member hingedly connected to one of the first wall member, the second wall member, the third wall member, and the fourth wall member, such that when the bottom member is parallel to the contact member, the volume is substantially enclosed;

a first aperture defined by an opening in the contact member;

a second aperture defined by a first opening in the first wall wherein the first aperture and the second aperture are facing in different lateral directions;

a first cushion member and at least a second cushion member configured to be secured in at least a portion of the volume by the bottom member and the contact member such that one or more medical instruments inserted through either or both of the first aperture and the second aperture are inserted into one or both of the first cushion member and the second cushion member effectively securing the medical instrument within the cushion member;

a boundary septum positioned between the first cushion member and the second cushion member;

a top surface positioned adjacent the boundary septum, the top surface forming a covering for the second cushion member, wherein the combination of the boundary septum and the top surface provide an effective boundary to prevent a needle or other sharp device which is positioned in the second cushion member from extending from the second aperture to any other aperture in a manner that could result in the inadvertent puncture of the skin of a practitioner; and a lid hingedly connected to an edge of the contact member, wherein the lid is configured to cover the first aperture when in a closed configuration.

2. The apparatus of claim 1, further comprising a third aperture defined by a second opening in the first wall.

3. The apparatus of claim 1, wherein the lid includes a drape member configured to at least partially cover the second aperture.

4. The apparatus of claim 1, wherein the cushion is configured to absorb fluids.

5. A temporary instrument holder, the temporary instrument holder comprising:

a body, the body including a top instrument holder aperture positioned on the top surface of the temporary instrument holder and a lateral instrument holder aperture positioned on a side surface of the body wherein the top instrument holder aperture and the lateral instrument holder aperture are facing in different lateral directions;

an instrument holder cushion layer associated with the top instrument holder aperture and configured to receive and secure a medical instrument inserted through the top instrument holder aperture;

a lateral instrument holder cushion layer associated with the lateral instrument holder aperture, and configured to receive and secure a medical instrument inserted through the lateral instrument holder aperture;

a boundary septum positioned between the top instrument holder aperture and the lateral instrument holder aperture;

a top surface positioned adjacent the boundary septum, the top surface forming a covering for the lateral instrument holder cushion layer, wherein the combination of the boundary septum and the top surface provide an effective boundary to prevent a needle or other sharp device which is positioned in the lateral instrument holder aperture from extending from the lateral instrument holder aperture to any other aperture in a manner that could result in the inadvertent puncture of the skin of a practitioner;

a hinged bottom member which is selectively attachable to the body, wherein when the bottom member is attached to the body the bottom member secures the one or more cushions within the body, and wherein when the hinged bottom member is closed one or both apertures and one or both cushion layers are positioned so to allow the introduction and retainment of one or more medical instruments; and one or more margin supports configured to fill any gap between one or both of the instrument holder cushion layer and the lateral instrument holder cushion layer and one or both of the hinged bottom member and a sidewall of the body into which the cushion layer is positioned.

6. The apparatus of claim 5, wherein at least one of the cushions is located within the body and is secured within the body utilizing the bottom member.

7. The apparatus of claim 5, wherein at least one instrument holder aperture is defined by a surface of the body opposite the hinged bottom member.

8. The apparatus of claim 5, further comprising an expandable drape configured to at least partially close the lateral instrument holder aperture located in a side of the body.

9. The apparatus of claim 8, further comprising a lid configured to selectably cover the top instrument holder aperture, and wherein the expandable drape is attached to the lid.

10. The apparatus of claim 8, wherein the expandable drape is attached to the housing adjacent to a securement aperture located in a side of the body.

11. The apparatus of claim 5, further comprising at least one adhesive member attached to the apparatus and configured to removably secure the apparatus to a surface.

12. The apparatus of claim 5, further comprising a plurality of ridges configured to securely hold the one or more cushions in contact with the body.

13. The apparatus of claim 12, wherein at least one of the plurality of ridges extends from the hinged bottom member.

14. The apparatus of claim 12, wherein at least one of the plurality of ridges extends from the body.

* * * * *